US009259003B2

(12) United States Patent
Fischer et al.

(10) Patent No.: US 9,259,003 B2
(45) Date of Patent: Feb. 16, 2016

(54) INSECTICIDES BASED ON NEONICOTINOIDS AND SAFENERS

(75) Inventors: Reiner Fischer, Monheim (DE); Wolfram Andersch, Bergisch Gladbach (DE); Heike Hungenberg, Langenfeld (DE); Wolfgang Thielert, Odenthal (DE); Lothar Willms, Hofheim (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 1630 days.

(21) Appl. No.: 11/632,184

(22) PCT Filed: Jul. 18, 2005

(86) PCT No.: PCT/EP2005/007793
§ 371 (c)(1),
(2), (4) Date: Jun. 11, 2008

(87) PCT Pub. No.: WO2006/008110
PCT Pub. Date: Jan. 26, 2006

(65) Prior Publication Data
US 2008/0261810 A1    Oct. 23, 2008

(30) Foreign Application Priority Data

Jul. 20, 2004 (DE) .......... 10 2004 035 130
Nov. 18, 2004 (DE) .......... 10 2004 055 581

(51) Int. Cl.
| | | |
|---|---|---|
| *A01N 25/34* | (2006.01) | |
| *A01N 43/40* | (2006.01) | |
| *A01N 43/78* | (2006.01) | |
| *A01P 7/00* | (2006.01) | |
| *A01N 43/88* | (2006.01) | |
| *A01N 43/08* | (2006.01) | |
| *A01N 47/40* | (2006.01) | |
| *A01N 51/00* | (2006.01) | |

(52) U.S. Cl.
CPC ............... *A01N 47/40* (2013.01); *A01N 51/00* (2013.01)

(58) Field of Classification Search
CPC ... A01N 47/40; A01N 51/00; A01N 2300/00; A01N 25/32; A01N 41/06
USPC ............. 504/100; 514/341, 357, 365, 229.2, 514/342, 471
See application file for complete search history.

(56) References Cited

U.S. PATENT DOCUMENTS

| | | | |
|---|---|---|---|
| 6,251,827 B1 * | 6/2001 | Ziemer et al. ................. | 504/130 |
| 2003/0050194 A1 * | 3/2003 | Hopkinson et al. ........... | 504/363 |
| 2004/0023801 A1 | 2/2004 | Asrar et al. | |
| 2004/0118040 A1 * | 6/2004 | Asrar et al. .................... | 47/57.6 |

FOREIGN PATENT DOCUMENTS

| | | | | |
|---|---|---|---|---|
| JP | 2003-321310 | * 11/2003 | ............. | A01N 51/00 |
| JP | 2003-321310 A | * 11/2003 | ............. | A01N 51/00 |

OTHER PUBLICATIONS

Ebel, R.C., et al., "Phytotoxicity of the Systemic Insecticide Imidacloprid on Tomato and Cucumber in the Greenhouse," *Horttechnology* 10:144-147, American Society for Horticultural Science (2000).

Jonitz, A. and Leist, N., "Seed testing and the effect of insecticidal active ingredients on the germination and emergence of hybrid maize seed," *Pflanzenschutz-Nachrichten Bayer* 566:173-207, Bayer CropScience (2003).

Saayman-du Toit, A.E.J., "Phytotoxicity resulting from a combination of a pre-emergence herbicide and a pesticide seed dressing in maize (*Zea mays* L.)," *S. Afr. Tydskr. Plant Grond* 19:156-158, Pretoria: Bureau for Scientific Publications, Foundation for Education, Science and Technology (2002).

Patent Abstracts of Japan, English language translation for JP 2003-321310.

* cited by examiner

*Primary Examiner* — Ernst V Arnold
*Assistant Examiner* — Hong Yu
(74) *Attorney, Agent, or Firm* — Sterne, Kessler, Goldstein & Fox P.L.L.C.

(57) ABSTRACT

Insecticidal compositions, characterized by an effective amount of a combination of active compounds comprising (a) at least one compound of the formula (I)

$$\text{Het} \diagdown \underset{\underset{X}{\|}}{N} \diagup A \qquad (I)$$
$$\phantom{\text{Het} \diagdown }\ \overset{R}{|}$$

in which Het, A, R and X are as defined in the description, and
(b) at least one crop plant compatibility-improving compound from the group of compounds listed in the description,
which are used for controlling arthropods, and also methods for controlling arthropods by treating plants and their seed with the compositions.

13 Claims, No Drawings

INSECTICIDES BASED ON NEONICOTINOIDS AND SAFENERS

The invention relates to the use of insecticidally active combinations of active compounds which comprise firstly one or more compounds from the group of the neonicotinoids and secondly at least one crop plant compatibility-improving compound, for improved control of insects in various crops of useful plants.

It is known that compounds of the formula (I)

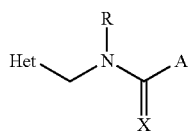

in which
Het represents a heterocycle which is in each case optionally mono- or polysubstituted by fluorine, chlorine, methyl or ethyl, which heterocycle is selected from the following group of heterocycles:
pyrid-3-yl, pyrid-5-yl, 3-pyridinio, 1-oxido-5-pyridinio, 1-oxido-5-pyridinio, tetra-hydrofuran-3-yl, thiazol-5-yl,
A represents $C_1$-$C_6$-alkyl, —N($R^1$)($R^2$) or S($R^2$),
in which
$R^1$ represents hydrogen, $C_1$-$C_6$-alkyl, phenyl-$C_1$-$C_4$-alkyl, $C_3$-$C_6$-cycloalkyl, $C_2$-$C_6$-alkenyl or $C_2$-$C_6$-alkynyl, and
$R^2$ represents $C_1$-$C_6$-alkyl, $C_2$-$C_6$-alkenyl, $C_2$-$C_6$-alkynyl, —C(=O)—$CH_3$ or benzyl,
R represents hydrogen, $C_1$-$C_6$-alkyl, $C_2$-$C_6$-alkenyl, $C_2$-$C_6$-alkynyl, —C(=O)—$CH_3$ or benzyl or together with $R^2$ represents the groups below:
—$CH_2$—$CH_2$—, —$CH_2$—$CH_2$—$CH_2$—, —$CH_2$—O—$CH_2$—, —$CH_2$—S—$CH_2$—, —$CH_2$—NH—$CH_2$—, —$CH_2$—N($CH_3$)—$CH_2$—, and
X represents N—$NO_2$, N—CN or CH—$NO_2$,
have insecticidal action (see, for example, EP-A1-192 606, EP-A2-580 533, EP-A2-376 279, EP-A2-235 725).

However, the compatibility of these compounds with the plants treated therewith, in particular with monocotyledonous crop plants, is not entirely satisfactory at all application rates and under all conditions.

Surprisingly, it has now been found that insecticides from the group of the neonicotinoids, when used together with the crop plant compatibility-improving compounds described below (safeners or antidotes), are unexpectedly well tolerated by crop plants and can be used particularly advantageously as broad-spectrum combination preparations for controlling insects.

Accordingly, the invention provides insecticidal compositions, comprising an active amount of at least
(a) one compound of the formula (I)

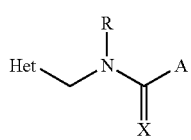

in which Het, A, R and X are as defined above, and
(b) at least one crop plant compatibility-improving compound from the following group of compounds:
4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinolin-8-oxy-acetate (cloquintocet-mexyl—cf. also related compounds in EP-A-86750, EP-A-94349, EP-A-191736, EP-A-492366), 3-(2-chlorobenzyl)-1-(1-methyl-1-phenyl-ethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino) ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)ethyl-3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane 4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinolin-8-oxyacetate, 4-allyloxybutyl 5-chloroquinolin-8-oxyacetate, 1-allyloxyprop-2-yl 5-chloroquinolin-8-oxyacetate, methyl 5-chloroquinoxalin-8-oxyacetate, ethyl 5-chloroquinolin-8-oxyacetate, allyl 5-chloroquinoxalin-8-oxyacetate, 2-oxoprop-1-yl 5-chloroquinolin-8-oxyacetate, diethyl 5-chloroquinolin-8-oxymalonate, diallyl 5-chloroquinoxalin-8-oxymalonate, diethyl 5-chloroquinolin-8-oxymalonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxybenzophenone, 1-bromo-4-chloromethylsulphonylbenzene, 1-[4-(N-2-methoxy-benzoylsulphamoyl)phenyl]-3-methylurea (alias N-(2-methoxybenzoyl)-4-[(methyl-aminocarbonyl)amino]benzenesulphonamide), 1-[4-(N-2-methoxybenzoylsulphamoyl)phenyl]-3,3-dimethylurea, 1-[4-(N4,5-dimethylbenzoylsulphamoyl)phenyl]-3-methylurea, 1-[4-

(N-naphthyl-sulphamoyl)phenyl]-3,3-dimethylurea, N-(2-methoxy-5-methylbenzoyl)-4-(cyclopropylamino-carbonyl)benzenesulphonamide,
and/or one of the following compounds (defined by general formulae)
of the general formula (IIa)

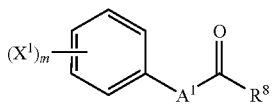

or of the general formula (IIb)

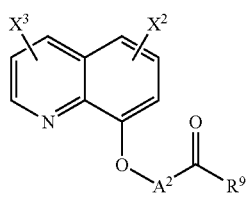

or of the formula (IIc)

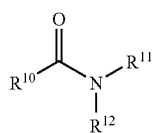

where
m represents a number of between 0 and 5,
$A^1$ represents one of the divalent heterocyclic groups outlined hereinbelow,

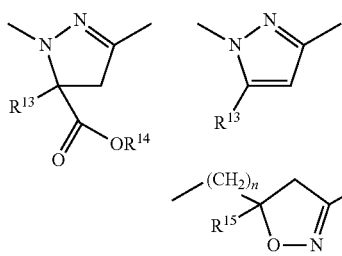

n represents a number of between 0 and 5,
$A^2$ represents alkanediyl having 1 or 2 carbon atoms which is optionally substituted by $C_1$-$C_4$-alkyl, $C_1$-$C_4$-alkoxy-carbonyl and/or $C_1$-$C_4$-alkenyloxy-carbonyl,
$R^8$ represents hydroxyl, mercapto, amino, $C_1$-$C_6$-alkoxy, $C_1$-$C_6$-alkylthio, $C_1$-$C_6$-alkylamino or di-($C_1$-$C_4$-alkyl)amino,
$R^9$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di-($C_1$-$C_4$-alkyl)amino,
$R^{10}$ represents $C_1$-$C_4$-alkyl which is optionally substituted in each case by fluorine, chlorine and/or bromine,
$R^{11}$ represents hydrogen, or represents $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, each of which is optionally substituted by fluorine, chlorine and/or bromine, or represents phenyl which is optionally substituted by fluorine, chlorine and/or bromine or $C_1$-$C_4$-alkyl,
$R^{12}$ represents hydrogen, or represents $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, each of which is optionally substituted by fluorine, chlorine and/or bromine, or represents phenyl which is optionally substituted by fluorine, chlorine and/or bromine or $C_1$-$C_4$-alkyl, or together with $R^{11}$ represents $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are bonded, form a 5- or 6-membered carbocycle,
$R^{13}$ represents hydrogen, cyano, halogen, or represents $C_1$-$C_4$-alkyl, $C_3$-$C_6$-cycloalkyl or phenyl, each of which is optionally substituted by fluorine, chlorine and/or bromine,
$R^{14}$ represents hydrogen, or represents $C_1$-$C_6$-alkyl, $C_3$-$C_6$-cycloalkyl or tri($C_1$-$C_4$-alkyl)silyl, optionally substituted by hydroxyl, cyano, halogen or $C_1$-$C_4$-alkoxy,
$R^{15}$ represents hydrogen, cyano, halogen, or represents $C_1$-$C_4$-alkyl, $C_3$-$C_6$-cycloalkyl or phenyl, each of which is optionally substituted by fluorine, chlorine and/or bromine,
$X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy,
$X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy,
$X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy,
and/or the following compounds (defined by general formulae)
of the general formula (IId)

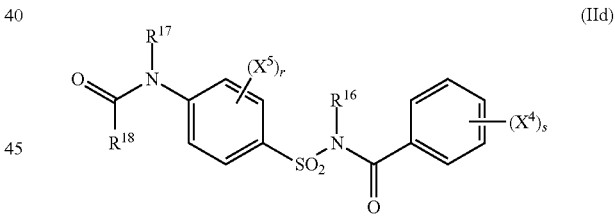

or of the general formula (IIe)

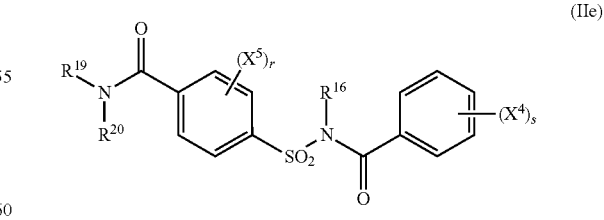

where
r and s represent a number of between 0 and 5,
$R^{16}$ represents hydrogen or $C_1$-$C_4$-alkyl,
$R^{17}$ represents hydrogen or $C_1$-$C_4$-alkyl,
$R^{18}$ represents hydrogen, or represents $C_1$-$C_6$-alkyl, $C_1$-$C_6$-alkoxy, $C_1$-$C_6$-alkylthio, $C_1$-$C_6$-alkylamino or di-($C_1$-$C_4$- alkyl)amino, each of which is optionally substituted by cyano, halogen or $C_1$-$C_4$-alkoxy, or represents $C_3$-$C_6$-cycloalkyl, $C_3$-$C_6$-cycloalkyloxy, $C_3$-$C_6$-cycloalkylthio or $C_3$-$C_6$-cycloalkylamino, each of which is optionally substituted by cyano, halogen or $C_1$-$C_4$-alkyl, $R^{19}$ represents hydrogen, or represents $C_1$-$C_6$-alkyl which is optionally substituted by cyano, hydroxyl, halogen or $C_1$-$C_4$-alkoxy, or represents $C_3$-$C_6$-alkenyl or $C_3$-$C_6$-alkynyl, each of which is optionally substituted by cyano or halogen, or represents $C_3$-$C_6$-cycloalkyl which is optionally substituted by cyano, halogen or $C_1$-$C_4$-alkyl, $R^{20}$ represents hydrogen, or represents $C_1$-$C_6$-alkyl which is optionally substituted by cyano, hydroxyl, halogen or $C_1$-$C_4$-alkoxy, or represents $C_3$-$C_6$-alkenyl or $C_3$-$C_6$-alkynyl, each of which is optionally substituted by cyano or halogen, or represents $C_3$-$C_6$-cycloalkyl which is optionally substituted by cyano, halogen or $C_1$-$C_4$-alkyl, or represents phenyl which is optionally substituted by nitro, cyano, halogen, $C_1$-$C_4$-alkyl, $C_1$-$C_4$-haloalkyl, $C_1$-$C_4$-alkoxy or $C_1$-$C_4$-haloalkoxy, or together with $R^{19}$ represents $C_2$-$C_6$-alkanediyl or $C_2$-$C_5$-oxaalkanediyl, each of which is optionally substituted by $C_1$-$C_4$-alkyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, for controlling insects.

In the definitions, the hydrocarbon chains, such as in alkyl, alkenyl or alkanediyl—are in each case straight-chain or branched—including in combination with heteroatoms, such as an alkoxy.

Optionally substituted radicals may, unless indicated otherwise, be mono- or polysubstituted, where in the case of polysubstitutions the substituents may be identical or different.

Depending inter alia on the nature of the substituents, the compounds of the formula (I) can be present as geometrical and/or optical isomers or isomer mixtures of varying composition which, if desired, can be separated in a customary manner. The invention provides both the pure isomers and the isomer mixtures, and their use, and compositions comprising them. However, hereinbelow, for the sake of simplicity, only compounds of the formula (I) are referred to, although what is meant are both the pure compounds and, if appropriate, any mixtures having varying proportions of isomeric compounds.

Preferred meanings of the radicals defined in formula (I) are given below.

Het preferably represents a heterocycle selected from the following group of heterocycles:
pyrid-3-yl, 2-chloropyrid-5-yl, 2-methylpyrid-5-yl, 1-oxido-3-pyridinio, 2-chloro-1-oxido-5-pyridinio, 2,3-dichloro-1-oxido-5-pyridinio, tetrahydrofuran-3-yl, 5-methyltetrahydro-furan-3-yl, 2-chlorothiazol-5-yl.

A preferably represents —N($R^1$)($R^2$) or S($R^2$).

$R^1$ preferably represents hydrogen, methyl, ethyl, n- or i-propyl, phenylmethyl, phenylethyl, cyclopropyl, cyclobutyl, cyclopentyl, cyclohexyl, ethenyl, 1-propenyl, 2-propenyl, ethynyl, 1-propynyl or 2-propynyl.

$R^2$ preferably represents methyl, ethyl, n- or i-propyl, n-, i-, s- or t-butyl, ethenyl, 1-propenyl, 2-propenyl, ethynyl, 1-propynyl, 2-propynyl, —C(=O)—$CH_3$ or benzyl.

R preferably represents hydrogen, methyl, ethyl, n- or i-propyl, ethenyl, 1-propenyl, 2-propenyl, ethynyl, 1-propynyl, 2-propynyl, —C(=O)—$CH_3$ or benzyl or together with $R^2$ preferably represents one of the following groups:

—$CH_2$—$CH_2$—, —$CH_2$—$CH_2$—$CH_2$—, —$CH_2$—O—$CH_2$—, —$CH_2$—S—$CH_2$—, —$CH_2$—NH—$CH_2$—, —$CH_2$—N($CH_3$)—$CH_2$—.

X preferably represents N—$NO_2$ or N—CN.

Het particularly preferably represents a heterocycle selected from the following group of heterocycles:
2-chloropyrid-5-yl, 2-methylpyrid-5-yl, 1-oxido-3-pyridinio, 2-chloro-1-oxido-5-pyridinio, 2,3-dichloro-1-oxido-5-pyridinio, tetrahydrofuran-3-yl, 5-methyltetrahydrofuran-3-yl, 2-chlorothiazol-5-yl.

A particularly preferably represents —N($R^1$)($R^2$).

$R^1$ particularly preferably represents hydrogen, methyl or ethyl.

$R^2$ particularly preferably represents methyl, ethyl, n- or i-propyl, n-, i-, s- or t-butyl, ethenyl, 1-propenyl, 2-propenyl, ethynyl, 1-propynyl, 2-propynyl, —C(=O)—$CH_3$ or benzyl.

R particularly preferably represents hydrogen, methyl, ethyl, or —C(=O)—$CH_3$ or together with $R^2$ particularly preferably represents one of the following groups:
—$CH_2$—$CH_2$—, —$CH_2$—$CH_2$—$CH_2$—, —$CH_2$—O—$CH_2$—, —$CH_2$—S—$CH_2$—.

Preferred compounds of the formula (I) which may be mentioned are the neonicotinoids listed in "The Pesticide Manual", 13th Edition, 2003 (British Crop Protection Council).

A very particularly preferred compound is imidacloprid of the formula known, for example, from EP A1 0 192 060.

A further very particularly preferred compound is clothianidin of the formula know, for example, from EP A2 0 376 279.

A further very particularly preferred compound is thiamethoxam of the formula known, for example, from EP A2 0 580 553.

A further very particularly preferred compound is thiacloprid of the formula

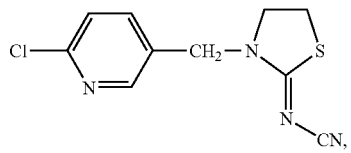

known, for example, from EP A2 0 235 725.

A further very particularly preferred compound is dinotefuran of the formula

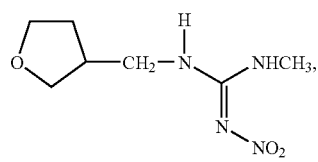

known, for example, from EP A1 0 649 845.

A further very particularly preferred compound is acetamiprid of the formula

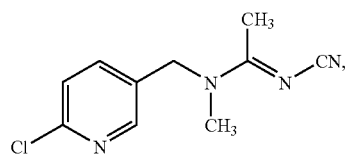

known, for example, from WO A1 91/04965.

A further very particularly preferred compound is nitenpyram of the formula

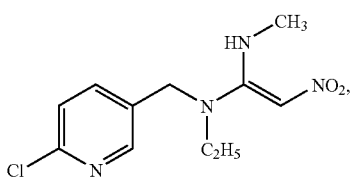

known, for example, from EP A2 0 302 389.

The general or preferred radical definitions or illustrations given above can be combined with one another as desired, i.e. including combinations between the respective ranges and preferred ranges.

Preference according to the invention is given to using the compounds of the formula (I) which contain a combination of the meanings listed above as being preferred (preferable).

Particular preference according to the invention is given to using the compounds of the formula (I) which contain a combination of the meanings listed above as being particularly preferred.

Very particular preference according to the invention is given to using the compounds of the formula (I) which contain a combination of the meanings listed above as being very particularly preferred.

Saturated or unsaturated hydrocarbon radicals, such as alkyl or alkenyl, can in each case be straight-chain or branched as far as this is possible, including in combination with heteroatoms, such as, for example, in alkoxy.

Unless indicated otherwise, optionally substituted radicals can be mono- or polysubstituted, where in the case of polysubstitution the substituents can be identical or different.

Depending inter alia on the nature of the substituents, the compounds of the formulae (IV-a), (IV-b), (IV-c), (IV-d) and (IV-e) can be present as geometrical and/or optical isomers or isomer mixtures of varying composition which, if desired, can be separated in a customary manner. In the compositions according to the invention, it is possible to employ both the pure isomers and the isomer mixtures and to utilize them according to the invention. However, hereinbelow, for the sake of simplicity, only compounds of the formulae (IV-a), (IV-b), (IV-c), (IV-d) and (IV-e) are referred to, although what is meant are both the pure compounds and, if appropriate, mixtures having varying proportions of isomeric compounds.

Preferred meanings of the groups listed above in connection with the crop plant compatibility-improving compounds ("herbicide safeners") of the formulae (IIa), (IIb), (IIc), (IId) and (IIe) are defined below.

m preferably represents the number 0, 1, 2, 3 or 4.

$A^1$ preferably represents one of the divalent heterocyclic groupings shown below

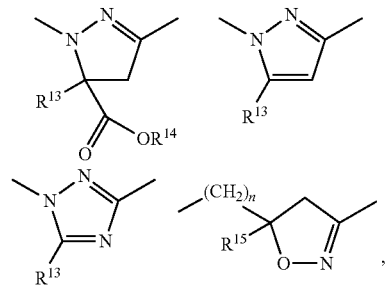

n preferably represents the number 0, 1, 2, 3 or 4.

$A^2$ preferably represents in each case optionally methyl-, ethyl-, methoxycarbonyl- or ethoxycarbonyl-substituted methylene or ethylene.

$R^8$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^9$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{10}$ preferably represents in each case optionally fluorine-, chlorine- and/or bromine-substituted methyl, ethyl, n- or i-propyl.

$R^{11}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl.

$R^{12}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl, or together with $R^{11}$ represents one of the radicals —$CH_2$—O—$CH_2$—$CH_2$— and —$CH_2$—$CH_2$—O—$CH_2$—$CH_2$— which are optionally substituted by methyl, ethyl, furyl, phenyl, a fused benzene ring or by two substituents which, together with the C atom to which they are attached, form a 5- or 6-membered carbocycle.

$R^{13}$ preferably represents hydrogen, cyano, fluorine, chlorine, bromine, or represents in each case optionally fluorine-, chlorine- and/or bromine-substituted methyl, ethyl, n- or i-propyl, cyclopropyl, cyclobutyl, cyclopentyl, cyclohexyl or phenyl.

$R^{14}$ preferably represents hydrogen, or represents in each case optionally hydroxyl-, cyano-, fluorine-, chlorine-, methoxy-, ethoxy-, n- or i-propoxy-substituted, methyl, ethyl, n- or i-propyl, n-, i-, s- or t-butyl.

$R^{15}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

r preferably represents one of the numbers 0, 1, 2, 3 or 4.
s preferably represents one of the numbers 0, 1, 2, 3 or 4.

$R^{16}$ preferably represents hydrogen, methyl, ethyl, n- or i-propyl.

$R^{17}$ preferably represents hydrogen, methyl, ethyl, n- or i-propyl.

$R^{18}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

$R^{19}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{20}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{19}$ represents in each case optionally methyl- or ethyl-substituted butane-1,4-diyl(trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

TABLE

Examples of the compounds of the formula (IIa)

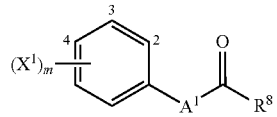

(IIa)

| Example No. | (positions) $(X^1)_m$ | $A^1$ | $R^8$ |
|---|---|---|---|
| IIa-1 | (2) Cl, (4) Cl | | $OCH_3$ |
| IIa-2 | (2) Cl, (4) Cl | | $OCH_3$ |
| IIa-3 | (2) Cl, (4) Cl | | $OC_2H_5$ |

TABLE-continued

Examples of the compounds of the formula (IIa)

(IIa)

| Example No. | (positions) $(X^1)_m$ | $A^1$ | $R^8$ |
|---|---|---|---|
| IIa-4 | (2) Cl, (4) Cl | 1-methyl-3-methyl-5-(methyl, ethoxycarbonyl)pyrazoline | $OC_2H_5$ |
| IIa-5 | (2) Cl | 1,3-dimethyl-5-phenylpyrazole | $OCH_3$ |
| IIa-6 | (2) Cl, (4) Cl | 1,3-dimethyl-5-phenylpyrazole | $OCH_3$ |
| IIa-7 | (2) F | 1,3-dimethyl-5-phenylpyrazole | $OCH_3$ |
| IIa-8 | (2) F | 1,3-dimethyl-5-(2-chlorophenyl)pyrazole | $OCH_3$ |
| IIa-9 | (2) Cl, (4) Cl | 1,3-dimethyl-5-trichloromethyl-1,2,4-triazole | $OC_2H_5$ |
| IIa-10 | (2) Cl, (4) $CF_3$ | 1-methyl-3-methyl-5-phenyl-1,2,4-triazole | $OCH_3$ |
| IIa-11 | (2) Cl | 1,3-dimethyl-5-(2-fluorophenyl)pyrazole | $OCH_3$ |
| IIa-12 | — | 5-methyl-3-methyl-5-phenyl-isoxazoline | $OC_2H_5$ |
| IIa-13 | (2) Cl, (4) Cl | 1,3-dimethyl-5-methylpyrazole | $OC_2H_5$ |
| IIa-14 | (2) Cl, (4) Cl | 1,3-dimethyl-5-isopropylpyrazole | $OC_2H_5$ |
| IIa-15 | (2) Cl, (4) Cl | 1,3-dimethyl-5-tert-butylpyrazole | $OC_2H_5$ |
| IIa-16 | (2) Cl, (4) Cl | 5-ethyl-3-methylisoxazoline | $OC_2H_5$ |
| IIa-17 | (2) Cl, (4) Cl | 3,5-dimethylisoxazoline | $OC_2H_5$ |
| IIa-18 | — | 5-methyl-3-methyl-5-phenylisoxazoline | OH |

Examples of the compounds of the formula (IIb) which are very particularly preferred as herbicide safeners according to the invention are listed in the table below.

TABLE

Examples of the compounds of the formula (IIb)

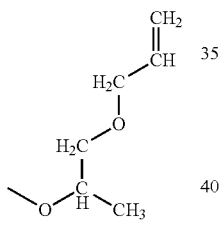

(IIb)

| Example No. | (Position) $X^2$ | (Position) $X^3$ | $A^2$ | $R^9$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | 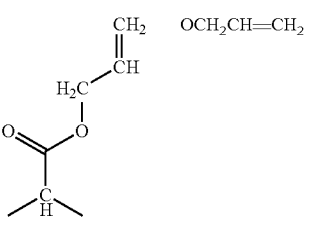 |
| IIb-13 | (5) Cl | — | 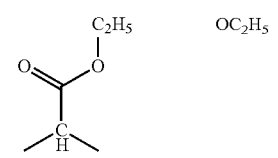 | $OCH_2CH=CH_2$ |
| IIb-14 | (5) Cl | — | 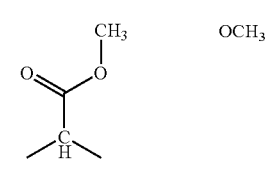 | $OC_2H_5$ |
| IIb-15 | (5) Cl | — | 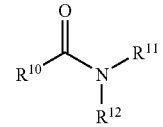 | $OCH_3$ |

TABLE

Examples of the compounds of the formula (IIc)

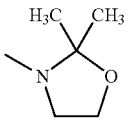

(IIc)

| Example No. | $R^{10}$ | $N(R^{11}, R^{12})$ |
|---|---|---|
| IIc-1 | $CHCl_2$ | $N(CH_2CH=CH_2)_2$ |
| IIc-2 | $CHCl_2$ | 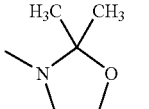 |
| IIc-3 | $CHCl_2$ | 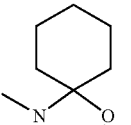 |
| IIc-4 | $CHCl_2$ | 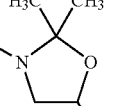 |
| IIc-5 | $CHCl_2$ | 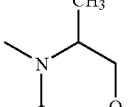 |
| IIc-6 | $CHCl_2$ | 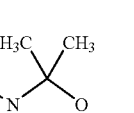 |
| IIc-7 | $CHCl_2$ |  |

Examples of the compounds of the formula (IIc) which are very particularly preferred as herbicide safeners according to the invention are listed in the table below.

Examples of the compounds of the formula (IId) which are very particularly preferred as herbicide safeners according to the invention are listed in the table below.

TABLE

Examples of the compounds of the formula (IId)

(IId)

| Example No. | $R^{16}$ | $R^{17}$ | $R^{18}$ | (positions) $(X^4)_s$ | (positions) $(X^5)_r$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H |  | (2) $OCH_3$ | — |
| IId-6 | H | H | $CH_3$ | (2) $OCH_3$ (5) $CH_3$ | — |
| IId-7 | H | H | $C_2H_5$ | (2) $OCH_3$ (5) $CH_3$ | — |
| IId-8 | H | H | $C_3H_7$-n | (2) $OCH_3$ (5) $CH_3$ | — |
| IId-9 | H | H | $C_3H_7$-i | (2) $OCH_3$ (5) $CH_3$ | — |
| IId-10 | H | H |  | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$-i | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$-i | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$-i | (2) $OCH_3$ (5) $CH_3$ | — |
| IId-20 | H | H |  | (2) $OCH_3$ (5) $CH_3$ | — |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2$—O—$CH_3$ | (2) $OCH_3$ | — |

Examples of the compounds of the formula (IIe) which are very particularly preferred as herbicide safeners according to the invention are listed in the table below.

TABLE

Examples of the compounds of the formula (IIe)

(IIe)

| Example No. | $R^{16}$ | $R^{19}$ | $R^{20}$ | (positions) $(X^4)_s$ | (positions) $(X^5)_r$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H |  | (2) $OCH_3$ | — |
| IIe-6 | H | $CH_3$ | $CH_3$ | (2) $OCH_3$ | — |
| IIe-7 | H | H | $CH_3$ | (2) $OCH_3$ (5) $CH_3$ | — |
| IIe-8 | H | H | $C_2H_5$ | (2) $OCH_3$ (5) $CH_3$ | — |
| IIe-9 | H | H | $C_3H_7$-n | (2) $OCH_3$ (5) $CH_3$ | — |
| IIe-10 | H | H | $C_3H_7$-i | (2) $OCH_3$ (5) $CH_3$ | — |
| IIe-11 | H | H |  | (2) $OCH_3$ (5) $CH_3$ | — |
| IIe-12 | H | $CH_3$ | $CH_3$ | (2) $OCH_3$ (5) $CH_3$ | — |

Preference according to the invention is given to combinations of active compounds comprising in each case at least one of the active compounds of the formula (I) selected from the group consisting of imidacloprid, thiamethoxam, clothianidin, thiocloprid, acetamiprid, nitenpyram and dinetofuran and in each case at least one of the safeners mentioned above.

Most preferred crop plant compatibility-improving compounds [component b)] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyr-diethyl.

Particularly preferred examples of the selective insecticidal and/or acaricidal combinations according to the invention of in each case one active compound of the formula (I) and in each case one of the safeners defined above are listed in the table below.

TABLE

Examples of combinations according to the invention

| Active compounds of the formula (I) | Safener |
|---|---|
| imidacloprid | cloquintocet-mexyl |
| imidacloprid | fenchlorazole-ethyl |
| imidacloprid | isoxadifen-ethyl |
| imidacloprid | mefenpyr-diethyl |

TABLE-continued

Examples of combinations according to the invention

| Active compounds of the formula (I) | Safener |
|---|---|
| imidacloprid | furilazole |
| imidacloprid | fenclorim |
| imidacloprid | cumyluron |
| imidacloprid | daimuron/dymron |
| imidacloprid | dimepiperate |
| imidacloprid | IIe-11 |
| imidacloprid | IIe-5 |
| clothianidin | cloquintocet-mexyl |
| clothianidin | fenchlorazole-ethyl |
| clothianidin | isoxadifen-ethyl |
| clothianidin | mefenpyr-diethyl |
| clothianidin | furilazole |
| clothianidin | fenclorim |
| clothianidin | cumyluron |
| clothianidin | daimuron/dymron |
| clothianidin | dimepiperate |
| clothianidin | IIe-11 |
| clothianidin | IIe-5 |
| thiamethoxam | cloquintocet-mexyl |
| thiamethoxam | fenchlorazole-ethyl |
| thiamethoxam | isoxadifen-ethyl |
| thiamethoxam | mefenpyr-diethyl |
| thiamethoxam | furilazole |
| thiamethoxam | fenclorim |
| thiamethoxam | Cumyluron |
| thiamethoxam | Daimuron/Dymron |
| thiamethoxam | Dimepiperate |
| thiamethoxam | IIe-5 |
| thiamethoxam | IIe-11 |
| thiacloprid | cloquintocet-mexyl |
| thiacloprid | fenchlorazole-ethyl |
| thiacloprid | isoxadifen-ethyl |
| thiacloprid | mefenpyr-diethyl |
| thiacloprid | furilazole |
| thiacloprid | fenclorim |
| thiacloprid | cumyluron |
| thiacloprid | daimuron/dymron |
| thiacloprid | dimepiperate |
| thiacloprid | IIe-11 |
| thiacloprid | IIe-5 |
| dinotefuran | cloquintocet-mexyl |
| dinotefuran | fenchlorazole-ethyl |
| dinotefuran | isoxadifen-ethyl |
| dinotefuran | mefenpyr-diethyl |
| dinotefuran | furilazole |
| dinotefuran | fenclorim |
| dinotefuran | cumyluron |
| dinotefuran | daimuron/dymron |
| dinotefuran | dimepiperate |
| dinotefuran | IIe-5 |
| dinotefuran | IIe-11 |
| acetamiprid | cloquintocet-mexyl |
| acetamiprid | fenchlorazole-ethyl |
| acetamiprid | isoxadifen-ethyl |
| acetamiprid | mefenpyr-diethyl |
| acetamiprid | furilazole |
| acetamiprid | fenclorim |
| acetamiprid | cumyluron |
| acetamiprid | daimuron/dymron |
| acetamiprid | dimepiperate |
| acetamiprid | IIe-5 |
| acetamiprid | IIe-11 |
| nitenpyram | cloquintocet-mexyl |
| nitenpyram | fenchlorazole-ethyl |
| nitenpyram | isoxadifen-ethyl |
| nitenpyram | mefenpyr-diethyl |
| nitenpyram | furilazole |
| nitenpyram | fenclorim |
| nitenpyram | cumyluron |
| nitenpyram | daimuron/dymron |
| nitenpyram | dimepiperate |
| nitenpyram | IIe-5 |
| nitenpyram | IIe-11 |

The compounds of the general formula (IIa) to be used as safeners are known and/or can be prepared by processes known per se (cf. WO-A-91/07874, WO-A-95/07897).

The compounds of the general formula (IIb) to be used as safeners are known and/or can be prepared by processes known per se (cf. EP-A-191736).

The compounds of the general formula (IIc) to be used as safeners are known and/or can be prepared by processes known per se (cf. DE-A-2218097, DE-A-2350547).

The compounds of the general formula (IId) to be used as safeners are known and/or can be prepared by processes known per se (cf. DE-A-19621522/U.S. Pat. No. 6,235,680).

The compounds of the general formula (IIe) to be used as safeners are known and/or can be prepared by processes known per se (vgl. WO-A-99/66795/U.S. Pat. No. 6,251,827).

Surprisingly it has now been found that the active compound combinations defined above of the compounds of the general formula (I) and safeners (antidotes) of group (b) listed above have good insecticidal activity whilst being tolerated very well by crop plants, and that they can be used for controlling pests in various crops.

Here, it has to be considered to be highly surprising that the compounds of group (b) listed above are capable of enhancing the insecticidal activity of the compounds of the formula (I) in some cases such that a synergistic effect is obtained.

Emphasis may be given here to the particularly advantageous effect of the particularly preferred combination partners of group (b), in particular with respect to application in cereal plants, such as, for example, wheat, oats, barley, triticale and rye, but also maize, millet, rice, sugar cane, soyabean, potatoes, cotton, oilseed rape, tobacco, hops and fruit plants (including pomaceous fruit, such as, for example, apples and pears, stone fruit, such as, for example, peaches, nectarines, cherries, plums and apricots, citrus fruit, such as, for example, oranges, grapefruits, limes, lemons, kumquats, mandarins and satsumas, nuts, such as, for example, pistachio nuts, almonds, walnuts and pecan nuts, tropical fruit, such as, for example, mangos, papayas, pineapples, dates and bananas, and grapevines).

The combinations can also be used for protecting vegetables. These include, inter alia, artichokes, aubergines, cauliflower, broccoli, green beans, peas, fennel, chicory, cucumbers, kohlrabi, lettuce, cress, leak, chard, carrots, bell peppers, rhubarb, beetroot, red cabbage, brussel sprouts, celery, beets, tomatoes, chestnuts, runner beans, scorzonera, maize, asparagus, table beet, spinach, white cabbage, savoy cabbage, onions, courgettes.

The combinations of active compounds can generally be used, for example, for the following plants:

Dicotyledonous crops of the genera: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cuburbita, Helianthus.*

Monocotyledonous crops of the genera: *Oryza, Zea, Triticum, Hordeum, Avena, Secale, Sorghum, Panicum, Saccharum, Ananas, Asparagus, Allium.*

However, the use of the combination of active compounds is by no means limited to these genera but equally also extends to other plants.

The advantageous effect of the crop plant compatibility of the combinations of active compounds is particularly strongly pronounced at certain concentration ratios. However, the weight ratios of the active compounds in the combinations of active compounds can be varied within relatively wide ranges. In general, 0.001 to 1000 parts by weight, preferably 0.01 to 100 parts by weight, particularly preferably 0.05 to 10 parts by weight and most preferably 0.07 to 1.5 parts by weight of one of the crop plant compatibility-improving compounds (antidotes/safeners) mentioned above under (b) are present per part by weight of active compound of the formula (I) or a salt thereof.

The mixtures according to the invention are particularly suitable for the treatment of seeds. Thus, most of the damage to crop plants which is caused by pests occurs as early as when the seed is infested during storage and after the seed is introduced into the soil, and during and immediately after germination of the plants. This phase is particularly critical since the roots and shoots of the growing plants are particularly sensitive and even minor damage can lead to the death of the whole plant. Protecting the seed and the germinating plant by the use of suitable compositions is therefore of particularly great interest.

The control of pests by treating the seed of plants has been known for a long time and is subject-matter of continuous improvements. However, the treatment of seed frequently entails a series of problems which cannot always be solved in a satisfactory manner. Thus, it is desirable to develop methods for protecting the seed and the germinating plant which dispense with the additional application of crop protection products after planting or after emergence of the plants. It is furthermore desirable to optimize the amount of active compound employed in such a way as to provide optimum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection products being employed.

The present invention therefore in particular also relates to a method for the protection of seed and germinating plants from attack by pests, by treating the seed with a composition according to the invention. The invention likewise relates to the use of the compositions according to the invention for the treatment of seed for protecting the seed and the germinating plant from pests. Furthermore, the invention relates to seed which has been treated with a composition according to the invention so as to afford protection from pests.

One of the advantages of the present invention is that the particular systemic properties of the compositions according to the invention mean that treatment of the seed with these compositions not only protects the seed itself, but also the resulting plant after emergence, from pests. In this manner, the immediate treatment of the crop at the time of sowing or shortly thereafter can be dispensed with.

A further advantage is the synergistically increased insecticidal activity of the compositions according to the invention in comparison with the respective individual active compound. This makes possible an optimization of the amount of active compound employed. Here, it has to be considered as being particularly advantageous that, by the presence of the mixing partners of group (b), the damage to the emerging plants that may be caused by the insecticidally active compounds used can, in a surprisingly effective manner, be limited or prevented altogether.

Furthermore, it must be considered as advantageous that the mixtures according to the invention can also be employed in particular in transgenic seed, the plants arising from this seed being capable of expressing a protein directed against pests. By treating such seed with the compositions according to the invention, certain pests can already be controlled by the expression of the for example insecticidal protein, and, surprisingly, the result in addition is a synergistically complemented activity together with the compositions according to the invention, which, again, increases the efficacy of the protection against attack by pests.

The compositions according to the invention are suitable for protecting seed of any plant variety which is employed in agriculture, in the greenhouse, in forests, in horticulture or in viticulture. In particular, this takes the form of seed of maize, peanut, canola, oilseed rape, poppy, olive, coconut, cacao, soya beans, cotton, beet (for example sugar beet and fodder beet), rice, millet, wheat, barley, oats, rye, sunflower, sugar cane or tobacco. The compositions according to the invention are likewise suitable for treating the seed of various vegetable species, such as, for example, broccoli, cauliflower, white cabbage, tomato, bell pepper, melon, courgette and cucumbers, or various pomaceous fruit, such as, for example, apple or pear. The treatment of the seed of maize, soya beans, cotton, wheat and canola or oilseed rape is of particular importance.

As already mentioned above, the treatment of transgenic seed with a composition according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

Within the scope of the present invention, the composition according to the invention is applied to the seed either alone or in suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. As a rule, it is preferable to apply the composition to the seed in the form of a suitable formulation. Suitable formulations and methods for the treatment of seed are known to the skilled worker and are described, for example, in the following documents: U.S. Pat. No. 4,272,417 A, 4,245,432 A, 4,808,430 A, 5,876,739 A, US 2003/0176428 A1, WO 2002/080675 A1, WO 2002/028186 A2.

The active compound combinations can be converted into the customary formulations, such as solutions, emulsions, wettable powders, suspensions, powders, dusts, pastes, soluble powders, granules, suspoemulsion concentrates, natural and synthetic materials impregnated with active compounds and microencapsulations in polymeric materials.

These formulations are produced in a known manner, for example by mixing the active compounds with extenders, that is, liquid solvents and/or solid carriers, optionally with the use of surface-active agents, that is, emulsifiers and/or dispersants and/or foam formers.

If the extender used is water, it is also possible to use for example organic solvents as auxiliary solvents. Suitable liquid solvents are mainly: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and ethers and esters thereof, ketones, such as acetone, methyl ethyl ketone, methyl isobutyl ketone or cyclohexanone, strongly polar solvents, such as dimethylformamide and dimethyl sulphoxide, and water.

Suitable solid carriers are:
for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable as solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable as emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable as dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95% by weight of active compound, preferably between 0.5 and 90%.

The combinations of active compounds are generally applied in the form of ready-to-use formulations. However, the active compounds contained in the combinations of active compounds may also be applied in the form of individual formulations which are mixed upon use, that is, in the form of tank mixes.

The combinations of active compounds, as such or in their formulations, may furthermore also be used as a mixture with other known herbicides, again with ready-to-use formulations or tank mixes being possible. A mixture with other known active compounds, such as fungicides, insecticides, acaricides, nematicides, attractants, steriliants, bactericides, bird repellents, growth substances, plant nutrients and soil conditioners is also possible. It may furthermore be advantageous for specific applications, in particular for the post-emergence method, to incorporate into the formulations plant-compatible mineral or vegetable oils (for example the commercial product "Rako Binol") or ammonium salts, such as, for example, ammonium sulphate or ammonium thiocyanate, as further additives.

The combinations of active compounds can be used as such, in the form of their formulations or the use forms which can be prepared from these formulations by further dilution, such as ready-to-use solutions, suspensions, emulsions, powders, pastes and granules. Application is effected in the customary manner, for example by watering, spraying, atomizing, dusting or broadcasting.

The application rates of the combination of active compounds can be varied within a certain range; they depend, inter alia, on the weather and the soil factors. In general, the application rates are from 0.005 to 5 kg per ha, preferably from 0.01 to 2 kg per ha, particularly preferably from 0.05 to 1.0 kg per ha.

The combinations of active compounds can be applied before and after emergence of the plants, i.e. by the pre-emergence and the post-emergence method.

Depending on their properties, the safeners to be used can be employed for pretreating the seed of the crop plant (seed dressing) or be incorporated into the seed furrows before sowing or, together with the herbicide, be applied before or after emergence of the plants.

The combinations of active compounds are suitable for controlling animals pests, preferably arthropods and nematodes, in particular insects and arachnids, encountered in agriculture. They are effective against normally sensitive and resistant species and against all or individual stages of development. The abovementioned pests include:

From the order of the Isopoda, for example, *Oniscus asellus, Armadillidium vulgare, Porcellio scaber*. From the order of the Diplopoda, for example, *Blaniulus guttulatus*. From the order of the Chilopoda, for example, *Geophilus carpophagus, Scutigera* spp. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Acheta domesticus, Gryllotalpa* spp., *Locusta migratoria migratorioides, Melanoplus* spp., *Schistocerca gregaria*. From the order of the Blattaria, for example, *Blatta orientalis, Periplaneta americana, Leucophaea maderae, Blattella germanica*. From the order of the Dermaptera, for example, *Forficula auricularia*. From the order of the Isoptera, for example, *Reticulitermes* spp. From the order of the Phthiraptera, for example, *Pediculus humanus corporis, Haematopinus* spp., *Linognathus* spp., *Trichodectes* spp., *Damalinia* spp. From the order of the Thysanoptera, for example, *Hercinothrips femoralis, Thrips tabaci, Thrips palmi, Frankliniella occidentalis*. From the order of the Heteroptera, for example, *Eurygaster* spp., *Dysdercus intermedius, Piesma quadrata, Cimex lectularius, Rhodnius prolixus, Triatoma* spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis porni, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus, Nilaparvata lugens, Aonidiella aurantii, Aspidiotus hederae, Pseudococcus* spp., *Psylla* spp. From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnis-*

*tis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus*. From the order of the Hymenoptera, for example, *Diprion* spp., *Hoplocampa* spp., *Lasius* spp., *Monomorium pharaonis, Vespa* spp. From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp. From the order of the Siphonaptera, for example, *Xenopsylla cheopis, Ceratophyllus* spp.

From the class of the arachnids, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

When used as insecticides, the combinations of active compounds can furthermore be present, in their commercial formulations and in the use forms prepared from these formulations, as a mixture with further synergists. Synergists are compounds which enhance the activity of the active compounds, without it being necessary for the added synergist to be active for its part.

The content of active compounds of the use forms prepared from the commercial formulations may vary within wide ranges. The concentration of active compounds of the use forms may be from 0.0000001 to 95% by weight of active compound and is preferably from 0.0001 to 1% by weight.

Application is carried out in a customary manner adapted to the use forms.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeder's certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes and cuttings. The combinations according to the invention are in particular also suitable for treating the seed of the crop plants mentioned above.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

As already mentioned above, it is possible to treat all plants and their parts according to the invention. In a preferred embodiment, wild plant species and plant varieties, or those obtained by conventional biological breeding methods, such as crossing or protoplast fusion, and parts thereof, are treated. In a further preferred embodiment, transgenic plants and plant varieties obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant varieties which are in each case commercially available or in use are treated according to the invention.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant varieties (i.e. those obtained by genetic engineering) which are preferred and to be treated according to the invention include all plants which, in the genetic modification, received genetic material which imparts particularly advantageous useful traits to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are particularly emphasized are the increased defense of the plants against insects by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), Knock-Out® (for example maize), StarLink® (for example maize), Boilgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant varieties having these or still-to-be-developed genetic traits, which plants will be developed and/or marketed in the future.

The plants listed and/or their seed can be treated according to the invention in a particularly advantageous manner with the active compound mixtures. The preferred ranges stated above for the mixtures also apply to the treatment of these plants and their seed. Particular emphasis is given to the treatment of plants and seed with the mixtures specifically mentioned in the present text.

The good insecticidal action of the active compound combinations according to the invention is illustrated by the examples below. While there may be weaknesses in the action of the individual active compounds, the combinations exhibit a surprising enhanced insecticidal action.

Formula for calculating the kill rate of a combination of two active compounds

The expected activity for a given combination of two active compounds can be calculated (cf. Colby, S. R.; "Calculating Synergistic and Antagonistic Responses of Herbicide Combinations", Weeds 15, pages 20-22, 1967):
if
X=the kill rate, expressed in % of the untreated control, when employing active compound A at an application rate of m ppm,
Y=the kill rate, expressed in % of the untreated control, when employing active compound B at an application rate of n ppm,
E=the kill rate, expressed in % of the untreated control, when employing active compounds A and B at application rates of m and n ppm, $$\text{then } E = X + Y - \frac{X \times Y}{100}$$

If the actual insecticidal kill rate is higher than the calculated one, the kill of the combination is superadditive, i.e. a synergistic effect is present. In this case, the kill rate that is actually observed has to be higher than the value, calculated using the formula above, for the expected kill rate (E).

EXAMPLE A

*Myzus persicae* Test

| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of active compound of the desired concentration.

After the desired period of time, the kill in % is determined. 100% means that all aphids have been killed; 0% means that none of the aphids have been killed. The determined kill rates are entered into Colby's formula.

In this test, for example, the following active compound combination according to the present application shows a synergistically enhanced activity compared to the active compounds applied on their own:

TABLE A1

*Myzus persicae* test

| Active compound | Concentration in ppm | Mortality in % after $1^d$ | |
|---|---|---|---|
| | | obs.* | cal.** |
| Clothianidin | 0.8 | 40 | |
| Isoxadifen-E WG 50 | 100 | 0 | |
| | | obs.* | cal.** |
| Clothiandin + Isoxadifen-E WG 50 (1:125) | 0.8 + 100 | 75 | 40 |
| Mefenpyr-diethyl WP 20 | 100 | 0 | |
| | | obs.* | cal.** |
| Clothianidin + Mefenpyr-diethyl WP 20 (1:125) | 0.8 + 100 | 60 | 40 |

*obs. = observed value
**cal. = value calculated using Colby's formula

TABLE A2

*Myzus persicae* test

| Active compound | Concentration in ppm | Mortality in % after $1^d$ | |
|---|---|---|---|
| | | obs.* | cal.** |
| Imidacloprid | 0.8 | 45 | |
| Isoxadifen-E WG 50 | 100 | 0 | |
| | | obs.* | cal.** |
| Imidacloprid + Isoxadifen-E WG 50 (1:125) | 0.8 + 100 | 85 | 45 |

*obs. = observed value
**cal. = value calculated using Colby's formula

TABLE A3

*Myzus persicae* test

| Active compound | Concentration in ppm | Mortality in % after $1^d$ | |
|---|---|---|---|
| | | obs.* | cal.** |
| Thiacloprid | 0.8 | 10 | |
| Isoxadifen-E WG 50 | 100 | 0 | |
| Thiacloprid + Isoxadifen-E WG 50 (1:125) | 0.8 + 100 | 30 | 10 |
| Mefenpyr-diethyl WP 20 | 100 | 0 | |
| Thiacloprid + Mefenpyr-diethyl WP 20 (1:125) | 0.8 + 100 | 55 | 10 |

*obs. = observed value
**cal. = value calculated using Colby's formula

EXAMPLE B

*Phaedon Cochleariae*—Larvae Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The determined kill rates are entered into Colby's formula.

In this test, the following active compound combination according to the present application shows a synergistically enhanced activity compared to the active compounds applied on their own:

TABLE B1

*Phaedon cochleariae* larvae test

| Active compound | Concentration in ppm | Mortality in % after $1^d$ | |
|---|---|---|---|
| | | obs.* | cal.** |
| Clothianidin | 4 | 40 | |
| (IIe-5) WP 20 | 200 | 0 | |
| Clothiandin + (IIe-5) WP 20 (1:50) | 4 + 100 | 15 | 0 |

*obs. = observed value
**cal. = value calculated using Colby's formula

TABLE B2

*Phaedon cochleariae* larvae test

| Active compound | Concentration in ppm | Mortality in % after $1^d$ | |
|---|---|---|---|
| | | obs.* | cal.** |
| Imidacloprid | 20 | 65 | |
| (IIe-5) WP 20 | 100 | 0 | |
| Imidacloprid + (IIe-5) WP 20 (1:5) | 20 + 100 | 90 | 65 |

*obs. = observed value
**cal. = value calculated using Colby's formula

TABLE B3

*Phaedon cochleariae* larvae test

| Active compound | Concentration in ppm | Mortality in % after $1^d$ | |
|---|---|---|---|
| | | obs.* | cal.** |
| Imidacloprid | 20 | 75 | |
| Isoxadifen-E WG 50 | 100 | 0 | |
| Imidacloprid + Isoxadifen-E WG 50 (1:5) | 20 + 100 | 100 | 75 |

*obs. = observed value
**cal. = value calculated using Colby's formula

TABLE B4

*Phaedon cochleariae* larvae test

| Active compound | Concentration in ppm | Mortality in % after $1^d$ | |
|---|---|---|---|
| | | obs.* | cal.** |
| Thiacloprid | 20 | 45 | |
| (IIe-5) WP 20 | 100 | 0 | |
| Thiacloprid + (IIe-5) WP 20 (1:5) | 20 + 100 | 80 | 45 |

*obs. = observed value
**cal. = value calculated using Colby's formula

EXAMPLE C

*Plutella xylostella* Test (Sensitive Strain)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamond back moth (*Plutella xylostella*, sensitive strain) while the leaves are still moist.

After the desired period of time, the kill in % is determined. 100% means that all caterpillars have been killed; 0% means that none of the caterpillars have been killed. The determined kill rates are entered into Colby's formula.

In this test, the following active compound combination according to the present application shows a synergistically enhanced activity compared to the active compounds applied on their own:

TABLE C1

Plutella xylostella test (sensitive strain)

| Active compound | Concentration in ppm | Mortality in % after $1^d$ | |
|---|---|---|---|
| Imidacloprid | 20 | 40 | |
| Isoxadifen-E WG 50 | 50 | 0 | |
| | | obs.* | cal.** |
| Imidacloprid + Isoxadifen-E WG 50 (1:2.5) | 20 + 50 | 75 | 40 |

*obs. = observed value
**cal. = value calculated using Colby's formula

TABLE C2

Plutella xylostella test (sensitive strain)

| Active compound | Concentration in ppm | Mortality in % after $1^d$ | |
|---|---|---|---|
| Thiacloprid | 20 | 80 | |
| Isoxadifen-ethyl WG 50 | 50 | 0 | |
| | | obs.* | cal.** |
| Thiacloprid + Isoxadifen-ethyl WG 50 (1:2.5) | 20 + 50 | 100 | 80 |

*obs. = observed value
**cal. = value calculated using Colby's formula

The invention claimed is:

1. A composition, comprising synergistic insecticidally effective amounts of:
   (a) at least one active compound selected from the group consisting of imidacloprid, clothianidin, thiacloprid, dinotefuran, and acetamiprid, and
   (b) at least one crop plant compatibility-improving compound selected from the group consisting of cloquintocet-mexyl, fenchlorazol-ethyl, isoxadifen-ethyl, mefenpyr-diethyl, furilazole, fenclorim, cumyluron, dimepiperate,

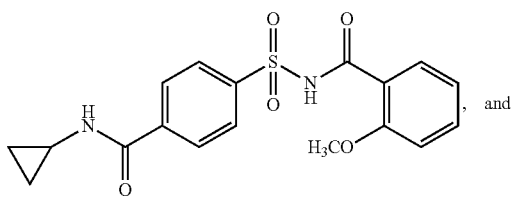

(IIe-5)

, and

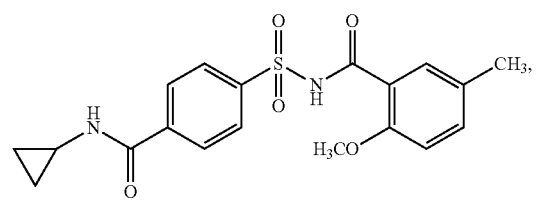

(IIe-11)

wherein the weight ratio of said at least one active compound to said at least one crop plant compatibility-improving compound is from 0.001:1 to 20:1.

2. A method for controlling arthropods, comprising contacting insects, arachnids, or their habitat, or combinations thereof, with a composition according to claim 1.

3. A method for protecting a seed against arthropods, comprising treating the seed with a composition according to claim 1.

4. The composition according to claim 1, wherein said at least one active compound is selected from the group consisting of imidacloprid, clothianidin, and thiacloprid.

5. The composition according to claim 1, wherein said at least one crop plant compatibility-improving compound is selected from the group consisting of cloquintocet-mexyl, isoxadifen-ethyl, mefenpyr-diethyl,

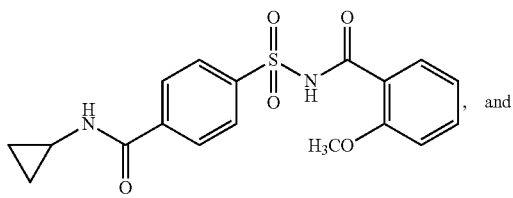

(IIe-5)

, and

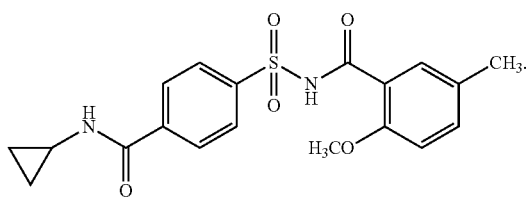

(IIe-11)

6. The composition according to claim 5, wherein the at least one crop plant compatibility-improving compound is

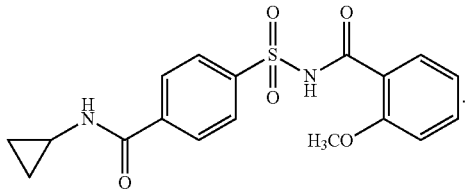

(IIe-5)

.

7. The composition according to claim 5, wherein the at least one crop plant compatibility-improving compound is

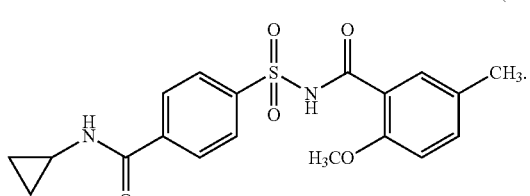

(IIe-11)

.

8. The composition according to claim 5, wherein the at least one crop plant compatibility-improving compound is cloquintocet-mexyl.

9. The composition according to claim 5, wherein the at least one crop plant compatibility-improving compound is mefenpyr-diethyl.

10. The composition according to claim 1, wherein the at least one active compound is clothianidin and the at least one crop plant compatibility-improving compound is selected from the group consisting of isoxadifen-ethyl, mefenpyr-diethyl, and

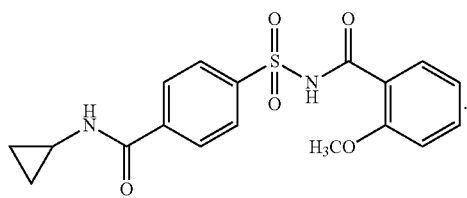

(IIe-5)

11. The composition according to claim 1, wherein the at least one active compound is imidacloprid and the at least one crop plant compatibility-improving compound is selected from the group consisting of isoxadifen-ethyl and

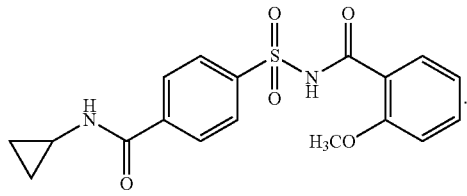

(IIe-5)

12. The composition according to claim 1, wherein the at least one active compound is thiacloprid and the at least one crop plant compatibility-improving compound is selected from the group consisting of isoxadifen-ethyl, mefenpyr-diethyl, and

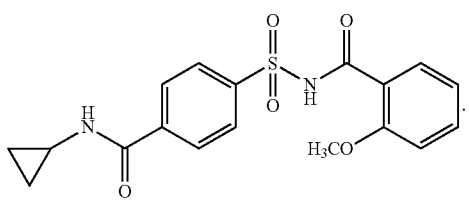

(IIe-5)

13. The composition according to claim 10, wherein the at least one crop plant compatibility-improving compound is

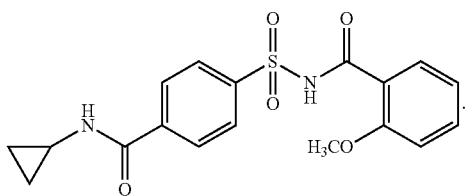

(IIe-5)

* * * * *